(12) United States Patent
Bedi

(10) Patent No.: US 11,723,775 B2
(45) Date of Patent: Aug. 15, 2023

(54) MAGNETIC MEDICAL IMPLANTS

(71) Applicant: Asheesh Bedi, Ann Arbor, MI (US)

(72) Inventor: Asheesh Bedi, Ann Arbor, MI (US)

(*) Notice: Subject to any disclaimer, the term of this patent is extended or adjusted under 35 U.S.C. 154(b) by 621 days.

(21) Appl. No.: 16/991,322

(22) Filed: Aug. 12, 2020

(65) Prior Publication Data

US 2022/0047396 A1 Feb. 17, 2022

(51) Int. Cl.
*A61F 2/40* (2006.01)
*A61F 2/46* (2006.01)
*A61F 2/30* (2006.01)

(52) U.S. Cl.
CPC .......... *A61F 2/4014* (2013.01); *A61F 2/4612* (2013.01); *A61F 2002/30079* (2013.01); *A61F 2002/30688* (2013.01); *A61F 2002/4022* (2013.01); *A61F 2002/4088* (2013.01)

(58) Field of Classification Search
CPC .... A61F 2002/30079; A61F 2002/4088; A61F 2002/4007; A61F 2/0018; A61F 2002/30052; A61F 2/4014; A61F 2002/4022; A61N 2/002; A61N 2/004; A61N 2/06; A61N 2/02
See application file for complete search history.

(56) References Cited

U.S. PATENT DOCUMENTS

| | | | | |
|---|---|---|---|---|
| 4,024,588 A * | 5/1977 | Janssen | ................ | A61F 2/4202 623/18.12 |
| 4,978,323 A * | 12/1990 | Freedman | ................ | A61N 2/06 623/23.49 |
| 5,176,618 A * | 1/1993 | Freedman | ................ | A61F 5/56 600/12 |
| 6,485,519 B2 * | 11/2002 | Meyers | ................ | A61F 2/3868 623/20.14 |
| 8,273,130 B2 | 9/2012 | Gradl | | |
| 8,590,537 B2 * | 11/2013 | Paraschac | ............... | A61F 5/566 600/12 |
| 9,707,105 B2 | 7/2017 | Cook et al. | | |
| 9,757,585 B2 * | 9/2017 | Bonutti | ..................... | A61F 2/30 |
| 9,956,080 B1 | 5/2018 | Howard | | |
| 10,500,071 B2 * | 12/2019 | Wang | ................... | A61B 5/4571 |
| 10,507,111 B2 * | 12/2019 | Johnson | ................... | A61F 2/30 |
| 2002/0032484 A1 * | 3/2002 | Hyde, Jr. | ................. | A61N 2/06 623/18.12 |
| 2003/0195633 A1 * | 10/2003 | Hyde, Jr. | ............... | A61B 17/68 623/18.12 |
| 2003/0236572 A1 * | 12/2003 | Bertram, III | .............. | A61F 2/32 623/18.12 |
| 2004/0059423 A1 * | 3/2004 | Barnes | ..................... | A61N 2/06 600/12 |
| 2004/0122470 A1 * | 6/2004 | Deem | ..................... | A61N 2/02 606/213 |

(Continued)

*Primary Examiner* — Alvin J Stewart
(74) *Attorney, Agent, or Firm* — Vorys, Sater, Seymour and Pease LLP

(57) ABSTRACT

A medical implant for a human shoulder joint includes a first magnetic implant fixed to the non-articular surface of the greater tuberosity of the human shoulder joint, and a second magnetic implant fixed to an outer surface and underside of the acromion of the human shoulder joint. At least one of the first and second magnetic implants generates a magnetic field that urges the first and second magnetic implants away from each other and thereby distracts the humeral head of the human shoulder joint from the acromion.

20 Claims, 3 Drawing Sheets

(56) References Cited

U.S. PATENT DOCUMENTS

| | | | |
|---|---|---|---|
| 2005/0251080 A1* | 11/2005 | Hyde, Jr. | A61F 2/3836 |
| | | | 602/26 |
| 2007/0100457 A1* | 5/2007 | Hyde | A61L 27/446 |
| | | | 623/18.12 |
| 2007/0209665 A1* | 9/2007 | Gillis | A61F 2/00 |
| | | | 128/848 |
| 2010/0331993 A1* | 12/2010 | Gradl | A61F 2/32 |
| | | | 623/23.4 |
| 2015/0005886 A1* | 1/2015 | Pinneo | A61F 2/32 |
| | | | 623/18.12 |
| 2017/0224495 A1* | 8/2017 | Rogachefsky | A61F 2/30 |
| 2017/0231768 A1* | 8/2017 | Gross | A61B 17/56 |
| | | | 623/18.12 |
| 2018/0014838 A1 | 1/2018 | Ning | |
| 2018/0221161 A1 | 8/2018 | Feffery | |
| 2020/0129299 A1 | 4/2020 | Huang et al. | |
| 2021/0030554 A1* | 2/2021 | Krettek | A61F 2/32 |

* cited by examiner

MAGNETIC MEDICAL IMPLANTS

BACKGROUND

Orthopedics is a medical subspecialty that treats disorders of the human body related to bones, muscles, ligaments, tendons, and joints. Treatment of orthopedic conditions has historically relied on casting and bracing, but with advancements in implantable materials and the development of improved joint replacement prostheses, orthopedics has increasingly become a surgical subspecialty. In the past several decades, numerous innovations have emerged in static mechanical design characteristics and new implantable materials used for fracture treatment and in total joint arthroplasties. Most of these improvements are directed to solutions to problems concerning wear and stability of joints as well as pain mitigation.

One improvement that has proven useful in orthopedic and musculoskeletal procedures is the use of implantable magnetic materials in joints, such as the knee, hip, and shoulder joints. Metals are often used as bearing surfaces in joint surface replacements, as implants for fracture and bone fixation, and for soft tissue-to-bone repair and reconstructive procedures. Magnetic materials and implants can be particularly advantageous for these applications, in that magnetic fields generated by magnetic implants can attract or repel one another with variable force based on selected polarity and strength of the generated fields. These forces may be used advantageously to create attractive forces that prevent implant dislocation, create repelling forces that maintain distraction of bearing surfaces (i.e., arthritis, rotator cuff arthropathy, minimize wear of bearing surfaces, etc.), or to help mitigate adverse forces on a healing repair or reconstruction.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is directed to medical implants and, more particularly, to magnetic implants that can be fixed to non-articular joint surfaces to prevent contact between adjacent bone structures.

Embodiments of the present disclosure describe use of strategically positioned and aligned magnetic implants that can have a transformative impact on orthopedics. In contrast to conventional joint repair and/or replacement, which often entail large and highly invasive procedures that carry a significant amount of risk and complication, the presently described magnetic implants can be introduced and installed in a minimally invasive fashion, such as via arthroscopic or arthroscopic-assisted techniques. Moreover, the location and strength of resulting magnetic fields can be titrated and personalized to patient-specific anatomy and injury (e.g., rotator cuff tear pattern and deficiencies in force couples). In some cases, applying the principles of the present disclosure may obviate the need for invasive joint arthroplasty or osteotomies to unload joints or resurface bearings. Instead, distractive forces provided by the presently described magnetic implants may offer similar or improved pain relief without the need for invasive replacements, with less alteration of anatomy, and more soft tissue preservation. The various embodiments discussed herein may be applied to, but are not limited to, rotator cuff arthropathy, superior capsular reconstruction, and supplementing or protecting a prosthetic implant or repair (soft tissue, soft tissue-to-bone, bone-to-bone repair).

Figure 1:
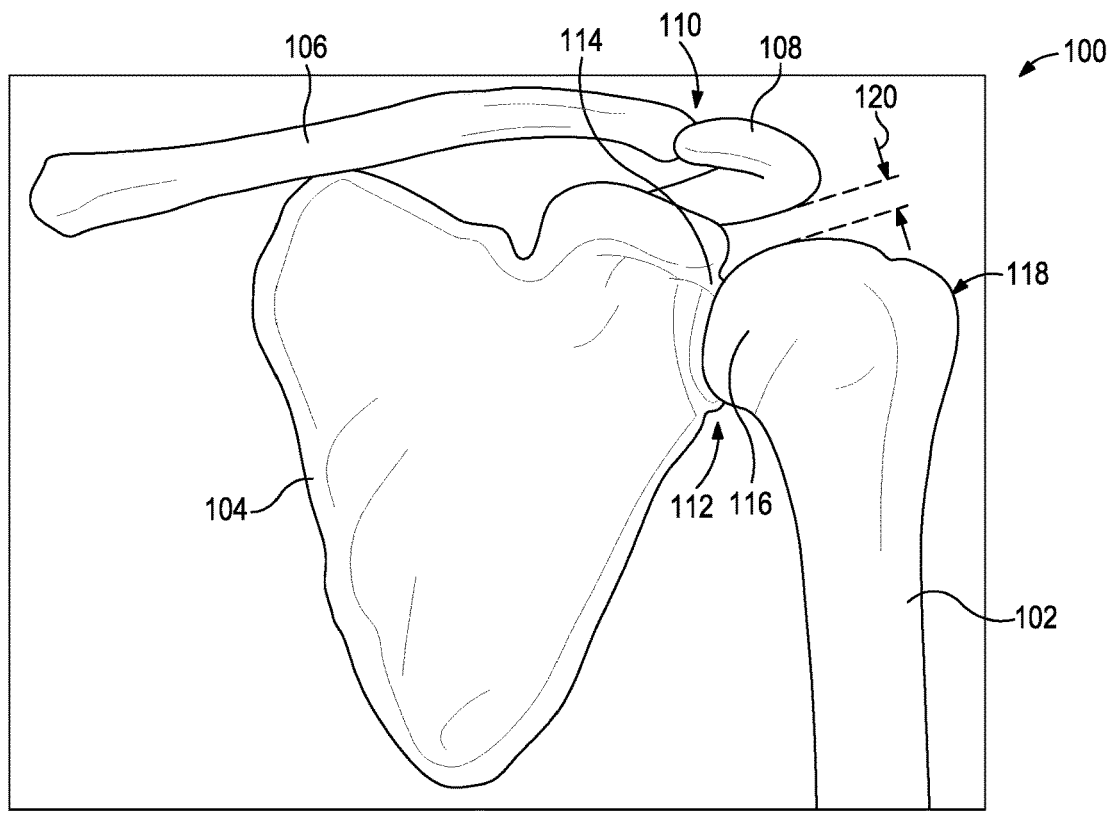
FIG. 1 is a schematic diagram of an example joint that may incorporate the principles of the present disclosure.

FIG. 1 is a schematic diagram of an example joint 100 that may incorporate the principles of the present disclosure. As depicted, the joint 100 comprises a human shoulder joint, but the principles of the present disclosure are equally applicable to other joints found in the human body including, but not limited to, knee, hip, elbow, wrist, ankle, and small joints of the feet and hands. Moreover, the principles of the present disclosure may be applicable to any location within the human body where portions of bone are disposed adjacent to each other, whether they are separate or functionally coupled with each other, and/or mechanically contacting each other due to anatomical reasons, non-anatomic reasons, and/or surgical treatments.

Major components of the joint 100 include the humerus 102, the scapula 104, the clavicle 106, and the acromion 108, where the clavicle 106 and the acromion 108 are joined at an acromioclavicular joint 110. The humerus 102 engages the scapula 104 at a glenohumeral joint 112 in a ball-and-socket relationship, where the glenoid 114 of the scapula 104 forms the socket and the humeral head 116 located at the top of the humerus 102 forms the ball that is partially received within the glenoid 114.

The glenohumeral joint 112 is held in place and operable with multiple force couples resulting from four muscles or tendons (not shown) that form connections between the top of the humerus 102 and the scapula 104. Upper and lower tendons, referred to as the supraspinatus and the teres minor tendons, respectively, control elevation of the glenohumeral joint 112, and front and back tendons, referred to as the infraspinatus and subscapularis tendons, control rotation of the glenohumeral joint 112. Each tendon arises from a rotator cuff muscle belly attached to the scapula 104 at particular locations and the opposing end is attached to the humerus 102. The supraspinatus, infraspinatus, and teres minor tendons (collectively referred to as the posterosuperior cuff) attach to the greater tuberosity 118, which forms part of the top of the humerus 102 adjacent the humeral head 116. The subscapularis inserts on the lesser tuberosity in the front of the humeral head. The shoulder tendons are collectively referred to as the "rotator cuff" of the shoulder, but the upper or supraspinatus tendon is often referred to as the "rotator cuff tendon" since most rotator cuff tears occur with this tendon.

In a healthy joint 100, articular cartilage covers the humeral head 116 and lines the inside surface of the glenoid 114 to provide a smooth, slippery surface for easy articulation of the joint 100. Accordingly, the humeral head 116 and the glenoid 114 are characterized as "articulating" or "articular" surfaces of the joint 100 that are covered in articular cartilage and hence designed to engage and rub against one another during typical shoulder operation. In contrast, other parts of the joint 100, such as the acromion 108 and the greater tuberosity 118, are characterized as "non-articulating" or "non-articular" surfaces not designed to contact each other during typical shoulder operation. The greater tuberosity 118 is normally not exposed and is the bony attachment point for the rotator cuff tendons. The acromion 108 is also an attachment point for other muscles around the shoulder, but does not normally articulate with the rotator cuff tendon, humeral head 116, or greater tuberosity 118. Accordingly, as defined herein, "non-articular surfaces" are non-bearing surfaces of a joint, or surfaces (of any soft tissue or bone) that only make contact with adjacent bone in a pathologic condition of tendon deficiency, such as rotator cuff deficiency, but do not otherwise comprise cartilage for joint engagement and are not designed for mutual engagement during typical joint operation.

The natural gap between the acromion 108 and the humeral head 116 is called the acromiohumeral interval 120. When the rotator cuff tendon(s) in the joint 100 become weakened, damaged or torn, especially the supraspinatus tendon, dynamic or static superior migration of the humeral head 116 toward the acromion 108 can result, thus reducing the distance of the acromiohumeral interval 120. With larger tears, rotator cuff arthropathy can develop and result in acromiohumeral articulation, where abnormal contact between the humeral head 116, the greater tuberosity 118, and the underside of the acromion 108 occurs. Acromiohumeral articulation can be a significant source of discomfort and disability in the joint 100.

In the past, rotator cuff arthropathy has been treated by undertaking various substantively invasive surgical procedures, such as joint arthroplasty or other procedures designed to replace all or a portion of the joint 100 with artificial implants. Such procedures, however, often result in limited longevity of artificial bearing surfaces, and suffer from the risk of loosening, instability, and failure of constrained implants with high loads. Moreover, soft tissue repairs and reconstructions related to joint arthroplasty (e.g., superior capsular reconstruction, patch-augmented repairs, interposition arthroplasty) can also fail, due to failed healing, inability to restore function, or an inability to mitigate high postoperative loads.

According to embodiments of the present disclosure, the acromiohumeral interval 120 may be at least partially maintained by placing one or more magnetic implants at strategic non-articular locations of the joint 100. By using repelling magnetic implants of the same polarity, distraction of adjacent non-articular surfaces may be achieved and maintained. As discussed herein, the location, strength, and dipole moment of the magnetic implant can be adjusted for patient-specific anatomy and pathology. Such implants could supplant current arthroplasties and other spacer devices that attempt to maintain a fixed inferior fulcrum (i.e., reverse shoulder arthroplasty), or may alternatively be used to augment these or other procedures designed to minimize acromiohumeral articulation; e.g., tuberoplasty, superior capsular reconstruction, partial or complete rotator cuff repair, acromial resurfacing procedures, balloon spacers, etc. Moreover, these implants may be prophylactically utilized to augment soft tissue repair procedures, such as rotator cuff repair, superior capsular reconstruction, etc., in which current failure rates are unacceptably high. In such applications, the magnetic implants may help mitigate early adverse postoperative loads and protect the repair to help improve outcomes from these procedures.

Figure 2A:
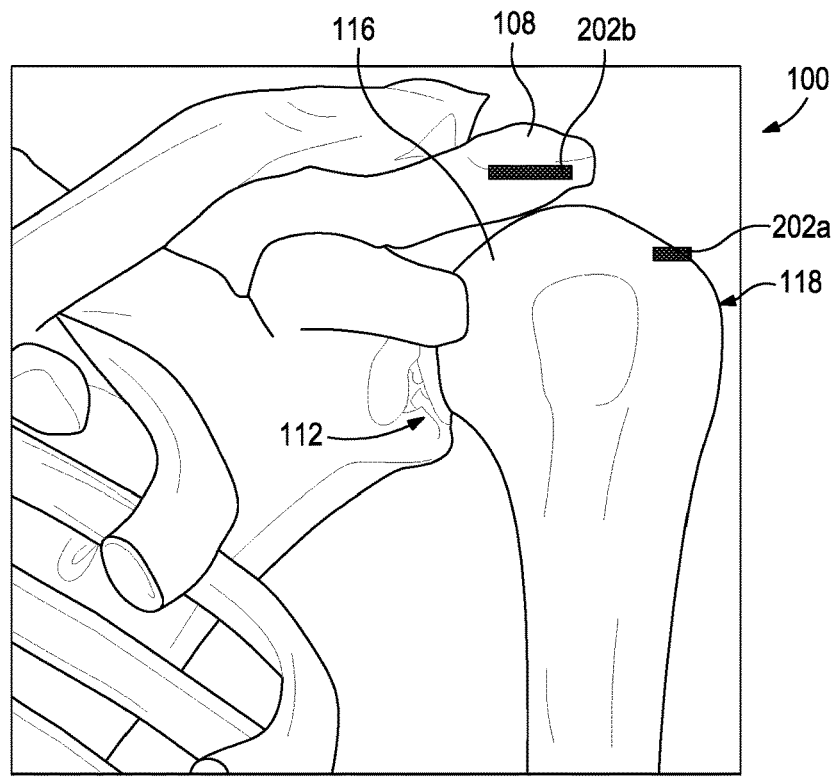
FIGS. 2A-2D are schematic views of the joint of FIG. 1 incorporating one or more principles of the present disclosure.
Figure 2B:
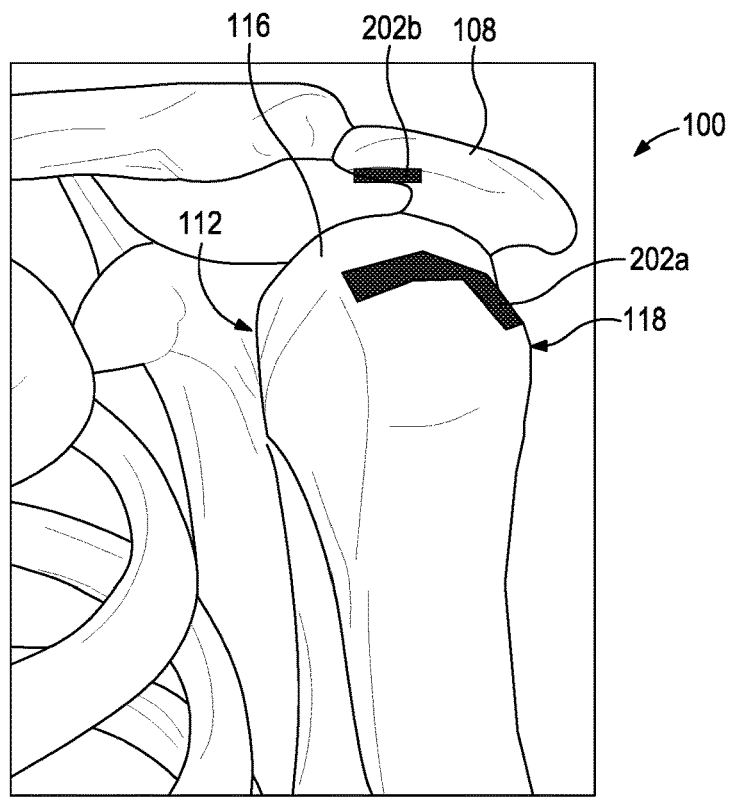
Figure 2C:
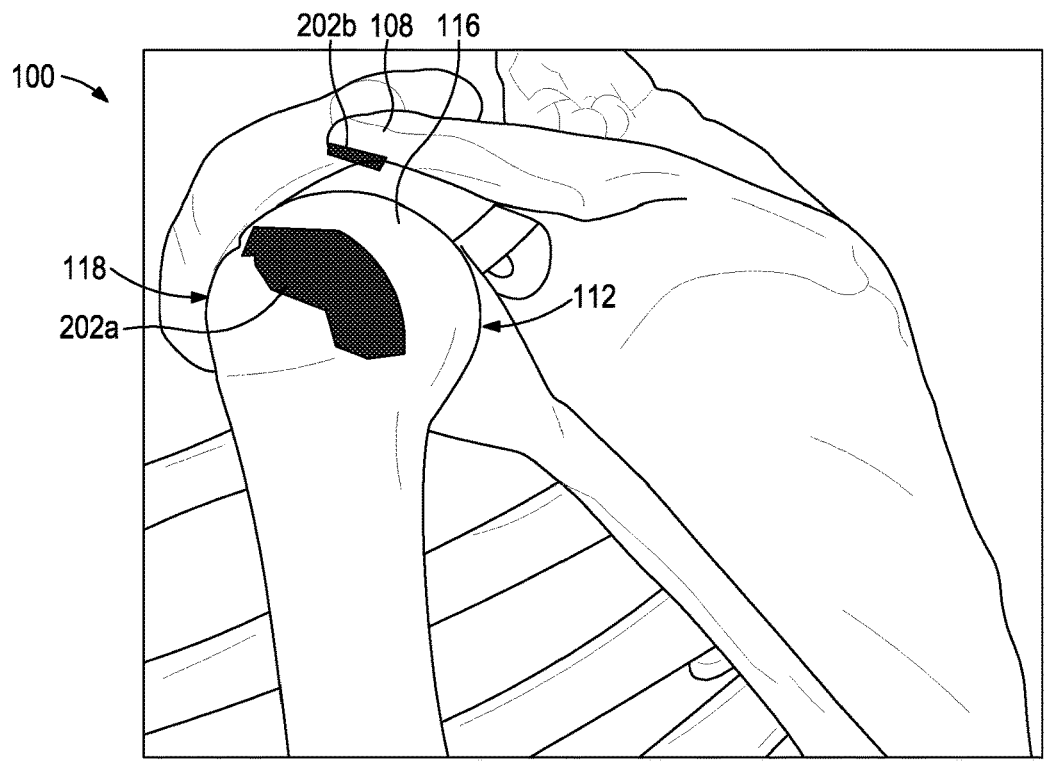
Figure 2D:
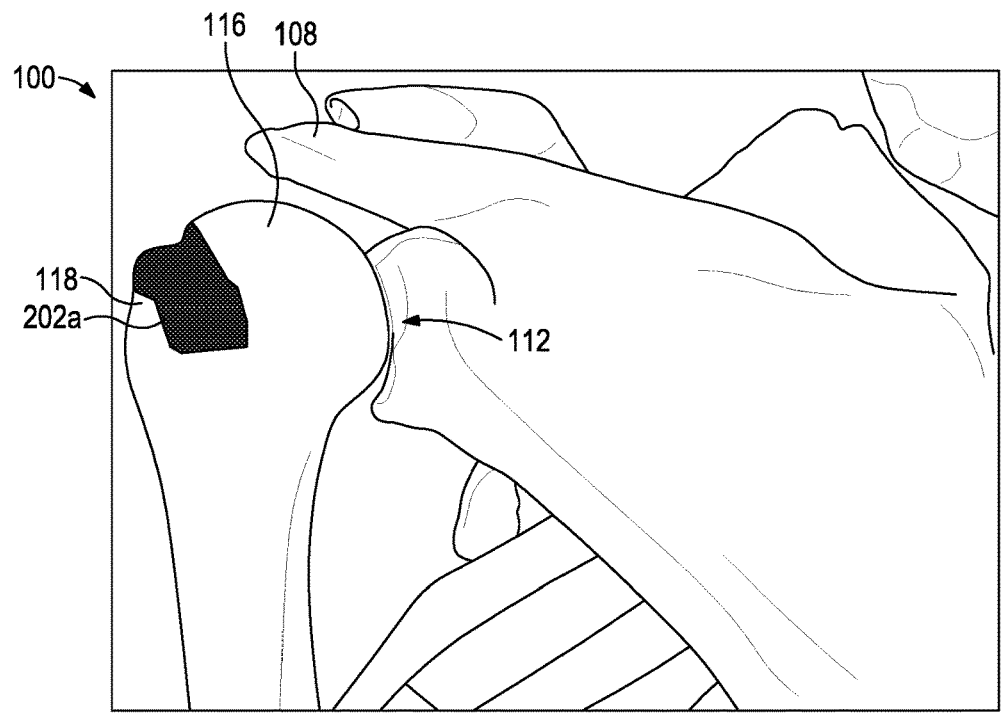

FIGS. 2A-2D are schematic views of the joint 100 in accordance with one or more principles of the present disclosure. More specifically, FIG. 2A is a front view of the joint 100, FIG. 2B is a view rotated about 60° to the right from the front view of FIG. 2A, FIG. 2C is a side view of the joint 100, and FIG. 2D is a back view of the joint 100. In the illustrated embodiment, a first magnetic implant 202a is coupled or otherwise fixed to the top of the greater tuberosity 118, which constitutes a first non-articular surface of the joint 100, and a second magnetic implant 202b is coupled or otherwise fixed to the underside of the acromion 108, which constitutes a second non-articular surface of the joint 100.

As the name suggests, the magnetic implants 202a,b are made of a magnetic material and, therefore, are either capable of generating a magnetic field or are otherwise susceptible to magnetic fields. Example magnetic materials include, but are not limited to, iron, soft ferrite, steel (e.g., stainless steel), cobalt, nickel, mu-metal, permalloy, rare-earth metal alloys, neodymium, samarium-cobalt, ceramic, alnico, magnesium, zinc polymer magnets, or any combination thereof. Polymer magnets are made from organic polymers and can include biocompatible and biodegradable polymers. Example magnetic materials may include any paramagnetic, diamagnetic, or ferromagnetic materials.

The magnetic materials contemplated herein may be magnetically active or magnetically passive. Magnetically active materials generate a magnetic field, while magnetically passive materials are susceptible to magnetic fields but do not actively generate a magnetic field. In one or more embodiments, the magnetic implants 202a,b may each be magnetically active and generate opposing magnetic fields with similar polarity. In other embodiments, however, one of the magnetic implants 202a,b may be magnetically active and may generate a magnetic field that repels the opposing magnetic implant 202a,b. In either scenario, the magnetic implants 202a,b will be repelled from one another and thereby constantly urge the greater tuberosity 118 away from the acromion 108. This creates an active distraction force between the acromion 108 and the humeral head 116 that facilitates humeral head 116 depression for improved glenohumeral joint 112 function, which can minimize pain resulting from acromiohumeral articulation and abrasion.

The magnetic implants 202a,b may be used in a variety of applications related to the joint 100, or any of the joints mentioned herein. In some embodiments, for example, the magnetic implants 202a,b may be used to supplement or protect a prosthetic implant. In such embodiments, the magnetic implants 202a,b may be used in conjunction with a total shoulder replacement to help prevent dynamic or static superior migration of an artificial humeral head toward the acromion 108. In other embodiments, the magnetic implants 202a,b may be used in conjunction with a torn rotator cuff. In applications where the rotator cuff is irreparable, the magnetic implants 202a,b may be fixed to opposing non-articular surfaces of the joint 100, such as the acromion 108 and the greater tuberosity 118. In applications where the rotator cuff is repairable, however, one or more magnetic anchors (active or passive) may be installed in the greater tuberosity 118 to secure the rotator cuff tendon and may be repelled by the second magnetic implant 202b fixed to the underside of the acromion 108. This application of the disclosure is described in more detail below with reference to FIG. 3.

As will be appreciated, every rotator cuff tear is unique. Accordingly, it is contemplated herein that the shape, the size, the strength/dipole moment, and the attachment location of each magnetic implant 202a,b may be selected or otherwise altered based on the pathology and anatomy of the patient. Consequently, the magnetic implants 202a,b can be provided, titrated, and attached in a manner that is customized to the specific pathologic condition of the patient.

In terms of shape, in some embodiments, one or both of the magnetic implants 202a,b may exhibit a polygonal cross-sectional shape (e.g., square, rectangular, pentagonal, etc.), or may alternatively comprise a disc having a circular or oval cross-section. In other embodiments, however, one or both of the magnetic implants 202a,b may exhibit a unique shape configured to mate with its particular non-articular attachment location. In such embodiments, for example, the first magnetic implant 202a may be at least partially cup-shaped or concave to enable a proper form fitting attachment to the outwardly protruding outer surface of the greater tuberosity 118. As best seen in FIGS. 2C and 2D, for example, the first magnetic implant 202a may extend about a large portion of the greater tuberosity 118. Similarly, in some embodiments, the second magnetic implant 202b may be bent, angled, or otherwise formed to enable a proper form fitting attachment to the uneven outer surface of the underside of the acromion 108.

In terms of size and strength of the magnetic implants 202a,b, smaller rotator cuff tears might require smaller magnetic implants 202a,b or otherwise implants that generate smaller (less intense) magnetic fields. In contrast, larger rotator cuff tears might require larger magnetic implants 202a,b or otherwise implants capable of generating larger (more intense) magnetic fields. In such embodiments, the size of the magnetic implant 202a,b may selected to obtain the desired magnetic strength. In other embodiments, however, the materials used for the magnetic implants 202a,b may be selected to obtain a more powerful magnetic field requiring less material.

In terms of attachment location of the magnetic implants 202a,b, force vectors are generated once the magnetic implants 202a,b are attached to corresponding non-articular surfaces. By placing the magnetic implants 202a,b in strategic locations of the joint 100, the generated force vectors can help supplement natural force couples of the joint 100 where the joint 100 may be lacking. In some embodiments, for example, and as best seen in FIGS. 2B and 2C, the second magnetic implant 202b may be attached to the anterior (front) surface or aspect of the acromion 108 on its underside since the humeral head 116 tends to shift in the anterior (front) and superior (up) directions (i.e., anterosuperior humeral escape) in the setting of posterosuperior rotator cuff deficiency. In such embodiments, the first magnetic implant 202a attached to the greater tuberosity 118 will help prevent anterior and superior migration of the humeral head 116. The first magnetic implant 202a attached to the greater tuberosity 118 may also be designed to extend medially onto the articular surface of the humeral head 116 to increase the surface area, strength, or vector of the magnetic field generated with the implant on the undersurface of the acromion 108.

Moreover, for smaller rotator cuff tears (i.e. involvement of only the supraspinatus tendon), the first magnetic implant 202a may be positioned on or extend across the anterior (front) portion of the greater tuberosity 118. For larger rotator cuff tears, the first magnetic implant 202a may be larger and positioned on or extend across the anterior (front) two-thirds (or more) of the greater tuberosity 118. If all of the rotator cuff tendons are detached, thus leaving the entire greater tuberosity 118 completely exposed, the first magnetic implant 202a may be formed and otherwise configured to cover the entire surface area of the greater tuberosity 118. Moreover, in some embodiments, the first magnetic implant 202a may be coupled to the greater tuberosity 118 with varying degrees of extension onto the surface area of the humeral head 116, as indicated above, while allowing preservation of the articular cartilage based on severity of disease. Such a design with variable extension of the implant medial to the greater tuberosity 118 and onto the humeral head 116 will increase the surface area and help to generate the ideal strength and/or vector of the magnetic field generated with the implant 202a on the undersurface of the acromion 108. This may prove useful in (i) maintaining anatomic humeral head 116 position, and (ii) improving best function of the force couple of the residual, intact rotator cuff musculature.

The magnetic implants 202a,b may be attached to non-articular outer surfaces of the joint 100 via a variety of attachment means, such as percutaneous mechanical fasteners or an adhesive. Example percutaneous mechanical fasteners include, but are not limited to, screws, tacks, suture anchors, sutures, staples, suspensory fixation devices, or any combination thereof. These may be locking or non-locking fixation to the magnetic implant and/or bone. Example magnet-to-bone or metal-to-bone fixation modalities that may be used include, but are not limited to guide-directed locking screws, percutaneous suspension buttons, suture configurations, anchor-based fixation constructs to bone, or any combination thereof. Examples of bone adhesives include synthetic adhesives (i.e., methacrylate and cyanoacrylates), biomimetic adhesives (i.e., bioceramics, frog or mussel glue, Tetranite™), bio-based adhesives (i.e., chitosan and/or hydroxyapatite, dextran, calcium carbonate, or fibrin-based adhesives), magnesium-based bone adhesives, and tapes.

As mentioned herein, one of the advantages of the present disclosure is its non-invasive nature. In most applications, only a few small incisions in the skin of the patient may be required to introduce, guide, and properly attach the magnetic implants 202a,b to non-articular outer surfaces of the bone via arthroscopic, arthroscopically-assisted, or mini-open techniques. Moreover, the magnetic implants 202a,b may be guided to the proper attachment location via a variety of non-invasive guidance methods and systems. In some embodiments, for example, one or more endoscopes (e.g., an arthroscope) with a camera may be introduced into the body via the small incisions to provide a user with a real-time positional view of the magnetic implants 202a,b. The endoscope(s) may help the operator (e.g., a doctor) accurately guide the magnetic implants 202a,b to the proper location in the joint 100 and further help the operator properly fixate the magnetic implants 202a,b.

In other embodiments, the magnetic implants 202a,b may be guided to the proper attachment location using one or more triangulating guides. In such embodiments, the incision in the patient's skin would only need to be large enough to introduce the triangulating guide with the magnetic implant 202a,b disposed on the end thereof. Triangulating guides can reproducibly and accurately target a fixation point on the magnetic implant for the placement of mechanical fasteners previously described. This can allow for minimally invasive targeting of fixation devices in or around the magnetic implants without an extensile exposure, analogous to triangulating drill guides used for reconstructive knee ligament surgery (i.e. anterior or cruciate ligament targeting guides). The triangulating guide with the magnetic implant on the targeted end is inserted into space, and the guide targets a drill to that location to achieve subsequent fixation with anchors, screws, tacks, sutures, etc.

Figure 3:
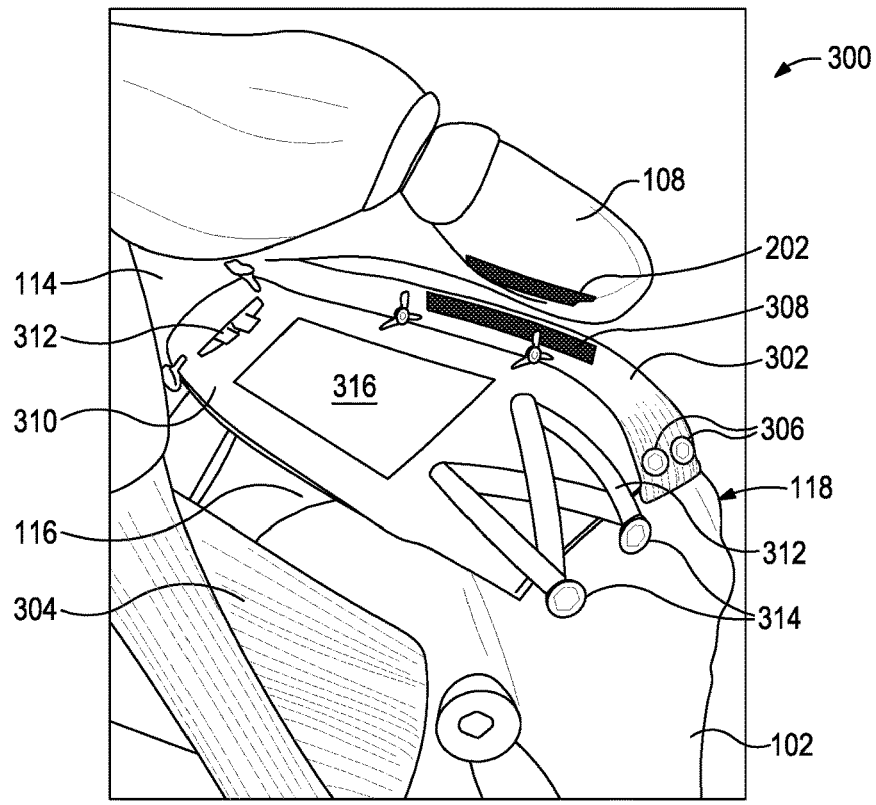
FIG. 3 is a schematic view of another example joint that incorporates one or more principles of the present disclosure.

FIG. 3 is a schematic view of another example joint 300 that may incorporate one or more principles of the present disclosure. Similar to the joint 100 of FIGS. 1 and 2A-2D, the joint 300 comprises a human shoulder joint that includes similar major component parts that will not be described again in detail. Moreover, similar to the joint 100, the embodiments described herein with reference to the joint 300 are equally applicable to other joints found in the human body. Consequently, the following description is not intended to be limited to applications only involving the shoulder, but are equally applicable to all other human joints, without departing from the scope of the disclosure.

In the illustrated embodiment, the supraspinatus tendon 302 and the infraspinatus tendon 304 are shown and attached to or near the top of the humerus 102. In this embodiment, the supraspinatus tendon 302, also referred to as the "rotator cuff" tendon, has been repaired by anchoring the end of the tendon 302 to the greater tuberosity using one or more magnetic implants 306 (two shown). In the illustrated embodiment, the magnetic implants 306 comprise anchors that are attached to and otherwise sunk into the greater tuberosity 118. The magnetic implants 306 may be made of a magnetically active material, such as stainless steel or iron, or may be magnetically passive like magnesium. In such embodiments, the second magnetic implant 202b attached to the underside of the acromion 108 will generate a repelling magnetic field that acts on the magnetic implants 306 to create a distraction force between the acromion 108 and the humeral head 116, and thereby facilitate humeral head 116 depression and maintenance of the acromiohumeral interval 120 (FIG. 1). The repelling forces generated between the acromion 108 and the greater tuberosity 118 may help maximize the chance that the rotator cuff repair heals by preventing inadvertent acromiohumeral contact and outlet impingement of the healing repair (abrasion).

In other embodiments, or in addition thereto, one or more magnetic implants 308 (one shown) may be attached to the top (e.g., bursal side) of the rotator cuff tendon 302, which may be considered a non-articular surface of the joint 300. The magnetic implant 308 may comprise, for example, a section of magnetic tape attached to the top of the rotator cuff tendon 302 using sutures, biodegradable tacks or staples, or an adhesive. In operation, the magnetic implant 308 may be magnetically active or passive and configured to interact with the second magnetic implant 202b to help facilitate humeral head 116 depression. The same principle would apply to patch augmentation of rotator cuff repairs, with fixation of the magnetic implant or tape to the bursal side of a soft tissue patch (a non-articular surface of allograft, xenograft, or biodegradable scaffolds).

In some embodiments, as briefly mentioned above, the principles of the present disclosure may be used in conjunction with superior capsular reconstruction of the human shoulder, which is a procedure commonly undertaken in patients with an irreparable or deficient rotator cuff tendon 302. In superior capsular reconstruction, as illustrated, a human allograft, xenograft, or an alternative soft tissue patch 310 (collectively referred to herein as "soft tissue patch 310") is attached between the greater tuberosity 118 and the superior glenoid 114. In typical operation, the soft tissue patch 310 acts as a tendon and helps prevents the humeral head 116 from migrating toward the acromion 108, and thereby prevents adjacent bone surfaces from coming into contact with one another, which could cause pain.

The soft tissue patch 310 may be secured in the joint 300 using sutures and/or suture anchors 312, or other suitable attachment means. In at least one embodiment, as illustrated, the soft tissue patch 310 may also be secured to the rotator cuff tendon 302 (e.g., the "stump"), if present. Moreover, one or more anchors 314 (two visible) are placed in both the greater tuberosity 118 and the superior glenoid 114 (only visible in the greater tuberosity 118) to secure the sutures 312. The anchors 314 may be made of a magnetic material, such as stainless steel, and may be magnetically passive. Consequently, the second magnetic implant 202b attached to the underside of the acromion 108 will generate a repelling magnetic field that acts on the anchors 314 to create a distraction force between the acromion 108 and the humeral head 116, and thereby facilitate humeral head 116 depression. Accordingly, the anchors 314 may be characterized and otherwise referred to herein as magnetic implants, similar in some respects to the first magnetic implant 202a (FIGS. 2A-2D).

In other embodiments, or in addition thereto, one or more magnetic implants 316 (one shown) may be attached to the top (e.g., bursal side) of the soft tissue patch 310, which may be considered a non-articular surface of the joint 300. Similar to the magnetic implant 308, the magnetic implant 316 may comprise a section of magnetic tape that may be attached to the top of the soft tissue patch 310 using sutures, biodegradable tacks or staples, or an adhesive. In operation, the magnetic implant 316 may be magnetically active or passive and configured to interact with the second magnetic implant 202b to help facilitate humeral head 116 depression.

Embodiments disclosed herein include:

A. A medical implant for a human shoulder joint that includes a first magnetic implant fixed to an outer surface of the greater tuberosity of the human shoulder joint, and a second magnetic implant fixed to an outer surface and underside of the acromion of the human shoulder joint, wherein at least one of the first and second magnetic implants generates a magnetic field that urges the first and second magnetic implants away from each other and thereby distracts the humeral head of the human shoulder joint from the acromion.

B. A medical implant for a joint that includes a first magnetic implant fixed to an outer surface of a first non-articular surface of the joint, and a second magnetic implant fixed to an outer surface of a second non-articular surface of the joint, wherein at least one of the first and second magnetic implants generates a magnetic field that urges the first and second magnetic implants away from each other and thereby distracts a first bone portion of the joint from a second bone portion of the joint.

C. A method includes making a minimally invasive incision in the skin of a patient at a location of a joint, inserting a first magnetic implant through the incision and fixing the first magnetic implant to an outer surface of a first non-articular surface of the joint, inserting a second magnetic implant through the incision and fixing the second magnetic implant to an outer surface of a second non-articular surface of the joint, generating a magnetic field with at least one of the first and second magnetic implants and thereby urging the first and second magnetic implants away from each other, and distracting a first bone portion of the joint from a second bone portion of the joint as the first and second magnetic implants are urged away from each other.

Each of embodiments A, B, and C may have one or more of the following additional elements in any combination: Element 1: wherein the first and second magnetic implants are made of a magnetic material selected from the group consisting of iron, soft ferrite, steel, cobalt, nickel, mu-metal, permalloy, a rare-earth metal alloy, neodymium, samarium-cobalt, ceramic, alnico, magnesium, zinc, a polymer magnet, and any combination thereof. Element 2: wherein the second magnetic implant is fixed to an anterior aspect of the underside of the acromion. Element 3: wherein the first magnetic implant is fixed to and extends across an anterior portion of the greater tuberosity. Element 4: wherein the first magnetic implant covers a majority or entirety of the greater tuberosity. Element 5: wherein the first magnetic implant extends partially onto the humeral head of the human shoulder joint. Element 6: wherein the first magnetic implant comprises one or more anchors that secure a tendon of the human shoulder joint to the greater tuberosity. Element 7: further comprising a third magnetic implant attached to a top of a tendon of the human shoulder joint. Element 8: wherein the first magnetic implant comprises one or more anchors that help secure a soft tissue patch extending between the greater tuberosity and the superior glenoid of the human shoulder joint. Element 9: further comprising a third magnetic implant attached to a human soft tissue patch extending between the greater tuberosity and the superior glenoid of the human shoulder joint.

Element 10: wherein the joint comprises a human joint selected from the group consisting of a shoulder, a knee, a hip, an elbow, a wrist, an ankle, and a small joint of a foot or a hand. Element 11: wherein the first and second magnetic implants exhibit a form fitting, concave shape matable with the outer surface of the first and second non-articular surfaces, respectively. Element 12: wherein the first and second magnetic implants are each magnetically active. Element 13: wherein the first magnetic implant comprises one or more anchors that secure a tendon of the joint to the first non-articular surface. Element 14: wherein the first non-articular surface comprises a tendon of the joint, the medical implant further comprising a third magnetic implant attached to a top of the tendon.

Element 15: further comprising determining placement of one or both of the first and second magnetic implants based on pathology of the patient. Element 16: further comprising select selecting a size or a strength of one or both of the first and second magnetic implants based on pathology of the patient. Element 17: further comprising viewing a real-time positional view of the first and second magnetic implants with an endoscope, and guiding one or both of the first and second magnetic implants to the non-articular surface based on the real-time positional view.

By way of non-limiting example, exemplary combinations applicable to A, B, and C include: Element 2 with any of Elements 3-9; Element 3 with Elements 4 or 5; Element 7 with any of Elements 1-6, 8 and 9; Element 11 with Element 12; Element 12 with Elements 13 and 14; Element 15 with either of Elements 16 or 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, right, and the like are used in relation to the illustrative embodiments as they are depicted in the figures, the upward direction being toward the top of the corresponding figure and the downward direction being toward the bottom of the corresponding figure.

What is claimed is:

1. A medical implant for a human shoulder joint, comprising:
    a first magnetic implant fixed to an outer surface of the greater tuberosity of the human shoulder joint; and
    a second magnetic implant fixed to an outer surface and underside of the acromion of the human shoulder joint,
    wherein at least one of the first and second magnetic implants generates a magnetic field that urges the first and second magnetic implants away from each other and thereby distracts the humeral head of the human shoulder joint from the acromion.

2. The medical implant of claim 1, wherein the first and second magnetic implants are made of a magnetic material selected from the group consisting of iron, soft ferrite, steel, cobalt, nickel, mu-metal, permalloy, a rare-earth metal alloy, neodymium, samarium-cobalt, ceramic, alnico, magnesium, zinc, a polymer magnet, and any combination thereof.

3. The medical implant of claim 1, wherein the second magnetic implant is fixed to an anterior aspect of the underside of the acromion.

4. The medical implant of claim 1, wherein the first magnetic implant is fixed to and extends across an anterior portion of the greater tuberosity.

5. The medical implant of claim 1, wherein the first magnetic implant covers a majority or entirety of the greater tuberosity.

6. The medical implant of claim 1, wherein the first magnetic implant extends partially onto the humeral head of the human shoulder joint.

7. The medical implant of claim 1, wherein the first magnetic implant comprises one or more anchors that secure a tendon of the human shoulder joint to the greater tuberosity.

8. The medical implant of claim 1, further comprising a third magnetic implant attached to a top of a tendon of the human shoulder joint.

9. The medical implant of claim 1, wherein the first magnetic implant comprises one or more anchors that help secure a soft tissue patch extending between the greater tuberosity and the superior glenoid of the human shoulder joint.

10. The medical implant of claim 1, further comprising a third magnetic implant attached to a human soft tissue patch extending between the greater tuberosity and the superior glenoid of the human shoulder joint.

11. A medical implant for a joint, comprising:
a first magnetic implant fixed to an outer surface of a first non-articular surface of the joint; and
a second magnetic implant fixed to an outer surface of a second non-articular surface of the joint,
wherein at least one of the first and second magnetic implants generates a magnetic field that urges the first and second magnetic implants away from each other and thereby distracts a first bone portion of the joint from a second bone portion of the joint.

12. The medical implant of claim 11, wherein the joint comprises a human joint selected from the group consisting of a shoulder, a knee, a hip, an elbow, a wrist, an ankle, and a small joint of a foot or a hand.

13. The medical implant of claim 11, wherein the first and second magnetic implants exhibit a form fitting, concave shape matable with the outer surface of the first and second non-articular surfaces, respectively.

14. The medical implant of claim 11, wherein the first and second magnetic implants are each magnetically active.

15. The medical implant of claim 11, wherein the first magnetic implant comprises one or more anchors that secure a tendon of the joint to the first non-articular surface.

16. The medical implant of claim 11, wherein the first non-articular surface comprises a tendon of the joint, the medical implant further comprising a third magnetic implant attached to a top of the tendon.

17. A method, comprising:
making a minimally invasive incision in the skin of a patient at a location of a joint;
inserting a first magnetic implant through the incision and fixing the first magnetic implant to an outer surface of a first non-articular surface of the joint;
inserting a second magnetic implant through the incision and fixing the second magnetic implant to an outer surface of a second non-articular surface of the joint;
generating a magnetic field with at least one of the first and second magnetic implants and thereby urging the first and second magnetic implants away from each other; and
distracting a first bone portion of the joint from a second bone portion of the joint as the first and second magnetic implants are urged away from each other.

18. The method of claim 17, further comprising determining placement of one or both of the first and second magnetic implants based on pathology of the patient.

19. The method of claim 17, further comprising select selecting a size or a strength of one or both of the first and second magnetic implants based on pathology of the patient.

20. The method of claim 17, further comprising:
viewing a real-time positional view of the first and second magnetic implants with an endoscope; and
guiding one or both of the first and second magnetic implants to the non-articular surface based on the real-time positional view.

* * * * *